US005676314A

United States Patent [19]

Brass et al.

[11] Patent Number: 5,676,314

[45] Date of Patent: Oct. 14, 1997

[54] LIMITED TIME USE SPRAYER

[75] Inventors: Richard Brass, Reinbeck, Iowa; Raymond F. Cracauer, Plymouth; Roland Beihl, Invergrove Heights, both of Minn.; Robert C. Hudson, Jr., Northbrook, Ill.

[73] Assignee: H.D. Hudson Manufacturing Company, Chicago, Ill.

[21] Appl. No.: 416,228

[22] Filed: Apr. 4, 1995

[51] Int. Cl.[6] .............................. B05B 9/08; A61M 11/02

[52] U.S. Cl. ........................... 239/373; 239/154; 222/401

[58] Field of Search .................................... 239/337, 373, 239/152, 154, 530; 222/401, 402, 530, 538; 220/675, 609, 608, 289

[56] References Cited

U.S. PATENT DOCUMENTS

| | | | |
|---|---|---|---|
| 2,211,823 | 8/1940 | Jepson | 222/401 |
| 2,550,157 | 4/1951 | Mazza | 222/538 |
| 3,002,698 | 10/1961 | Gallo | 239/569 X |
| 3,993,245 | 11/1976 | Smith | 239/154 |
| 4,214,674 | 7/1980 | Jones et al. | 222/401 |
| 4,372,455 | 2/1983 | Cochran | 220/675 |
| 4,805,814 | 2/1989 | Allen, Sr. | 222/538 |
| 5,072,884 | 12/1991 | Ellison et al. | 239/373 |
| 5,469,984 | 11/1995 | Kalkanis | 220/608 |
| 5,472,124 | 12/1995 | Martushev | 222/530 |
| 5,478,015 | 12/1995 | Black | 239/154 |

FOREIGN PATENT DOCUMENTS

| | | | |
|---|---|---|---|
| 678547 | 1/1964 | Canada | 239/333 |
| 716431 | 8/1965 | Canada | 239/333 |
| 526252 | 10/1921 | France | 239/373 |
| 9172 | 6/1889 | United Kingdom | 239/333 |
| 92/20587 | 11/1992 | WIPO | 220/609 |

*Primary Examiner*—Lesley D. Morris
*Attorney, Agent, or Firm*—Kane, Dalsimer, Sullivan, Kurucz, Levy, Eisele and Richard, LLP

[57] ABSTRACT

A sprayer includes a tank having a pump for pressurizing the liquid contents of the pump. The sprayer has a hose extending from the tank for receiving liquid directly from the pump, a spray control valve and discharge nozzle for directing the spray. One or more parts from the pump inlet to the discharge nozzle are adapted to fail after a certain period of time with reuse of the sprayer.

24 Claims, 5 Drawing Sheets

LIMITED TIME USE SPRAYER

BACKGROUND OF THE INVENTION

Garden and industrial sprayers are normally completely reusable and feature a pressure tank for the liquid solution to be dispensed having a sealable fill opening, an internally mounted piston/cylinder pump for pressurizing the tank interior, an outlet hose, a flow control valve associated with the hose, and an extension rod having a discharge nozzle. The tank is usually filled with the desired chemical in concentrated form and diluted by adding water to arrive at the desired solution for spraying. The chemical concentrate is purchased commercially from the desired source and may be contained in 1 gallon, 5 gallon or higher capacity bottles or containers.

SUMMARY OF THE INVENTION

A principal object of the present invention is to provide a limited time use sprayer that may be prefilled and is rendered non reusable and disposable after a certain limited period of use and/or time.

Another object is to provide a sprayer of the foregoing type which is sold and purchased as a complete package including a built in pump, outlet hose, spray control valve, rod extension and discharge nozzle.

A further object is to provide a sprayer of the foregoing type that is safe, cost effective and relatively easy to manufacture and which possesses a tank similar in appearance to the commercially available bottles or containers for chemical concentrates.

Still another object is to provide a sprayer of the foregoing type that requires only a single stroke of a piston cylinder pump assembly for supplying means for a spraying cycle.

A still further object is to provide a sprayer of the foregoing type that has the advantage of not requiring a tank capable of withstanding pressurization and consequently is intrinsically safe from overpressurization.

Other objects and advantages will become apparent from the following detailed description which is to be taken in conjunction with the accompanying drawings.

DETAILED DESCRIPTION

Figure 2:
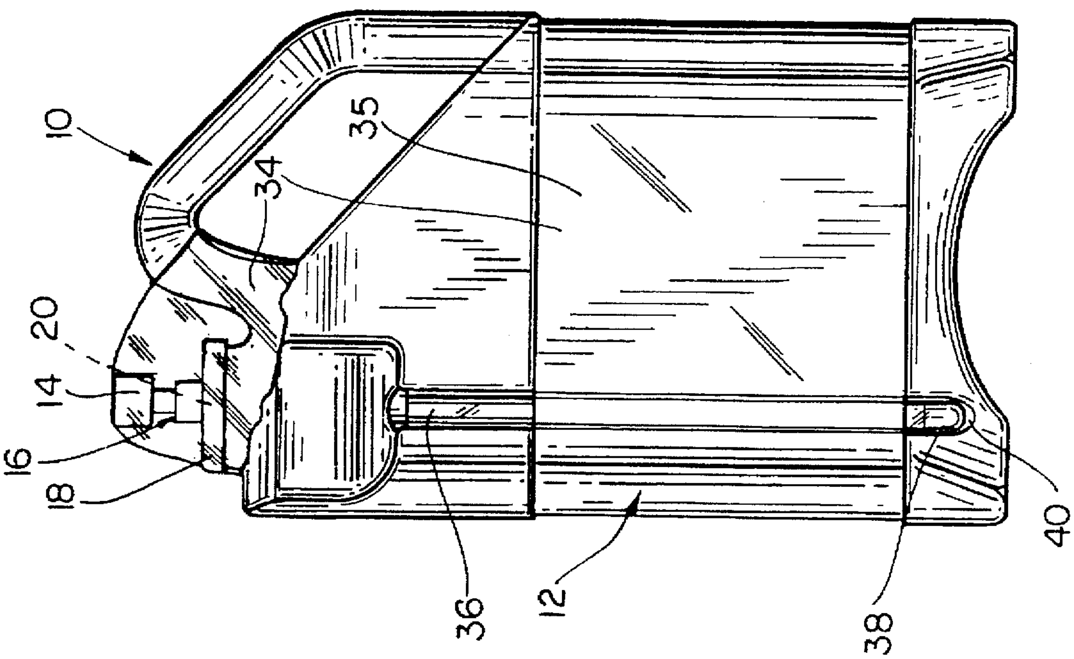
FIG. 2 is a rear elevational view thereof.
Figure 1:
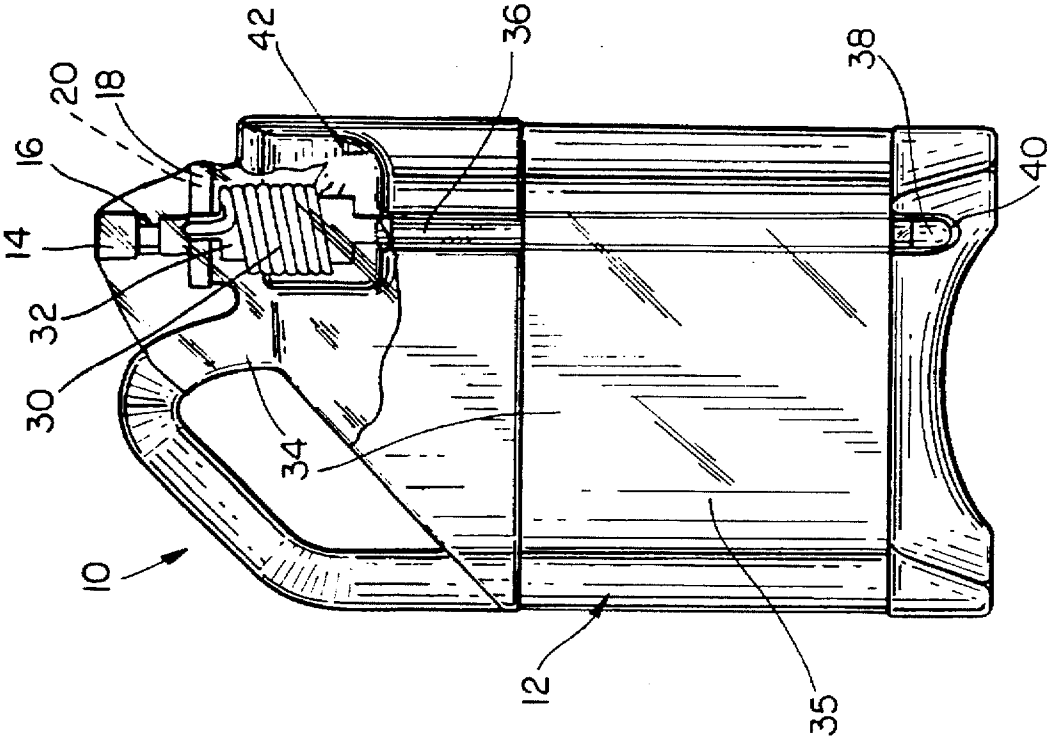
FIG. 1 is a front elevational view of the sprayer of this invention as commercially sold.
Figure 3:
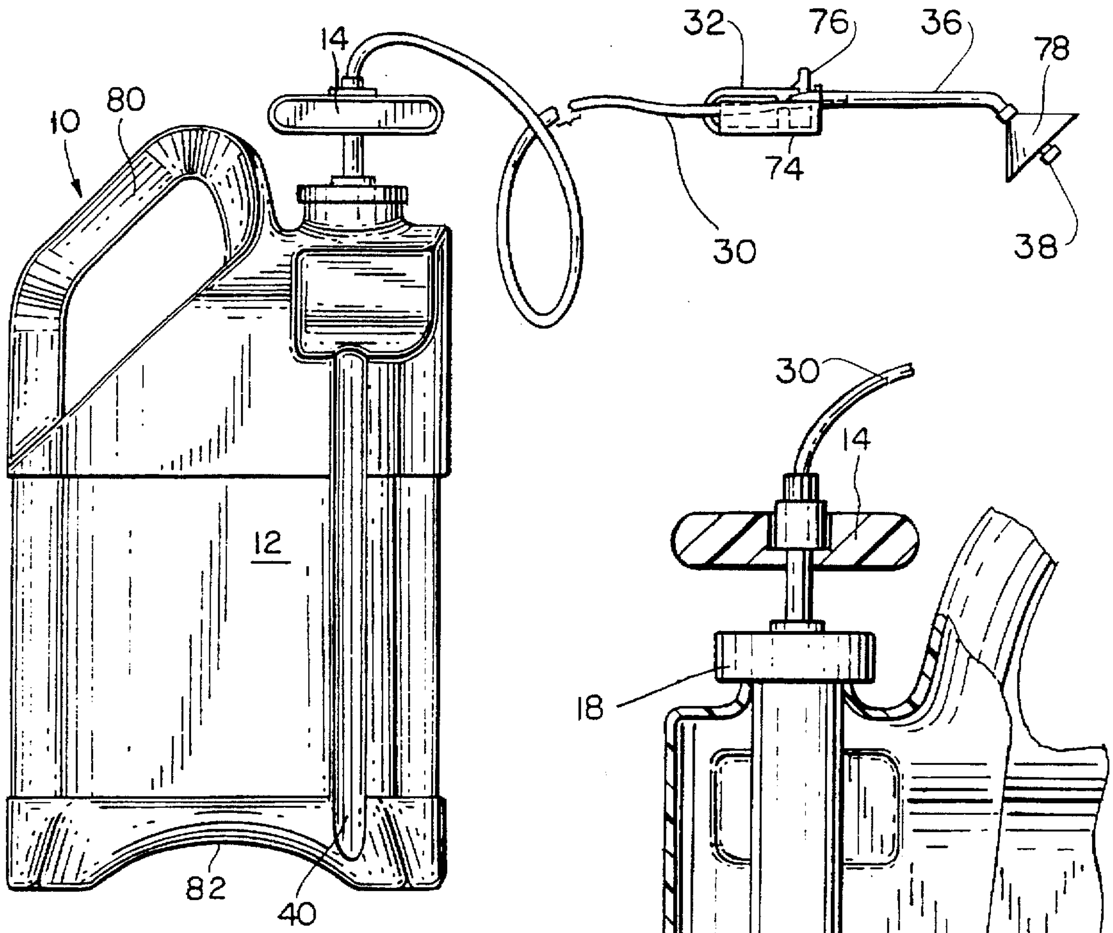
FIG. 3 is a front elevational view of the sprayer ready for use.
Figure 4:
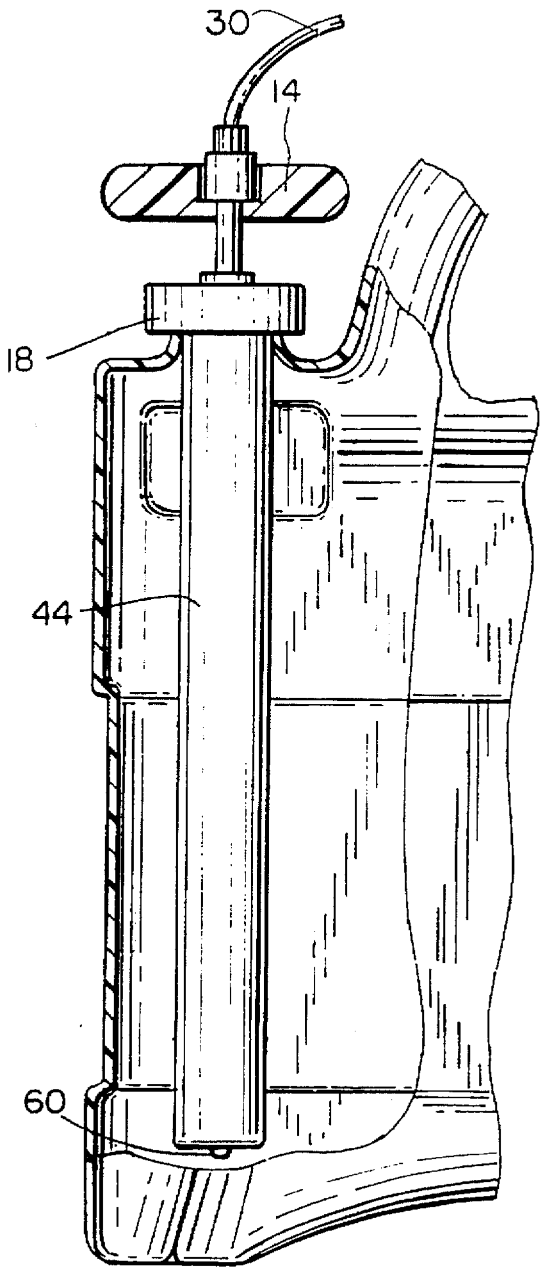
FIG. 4 is an enlarged fragmentary sectional view showing the pump assembly.
Figure 5:
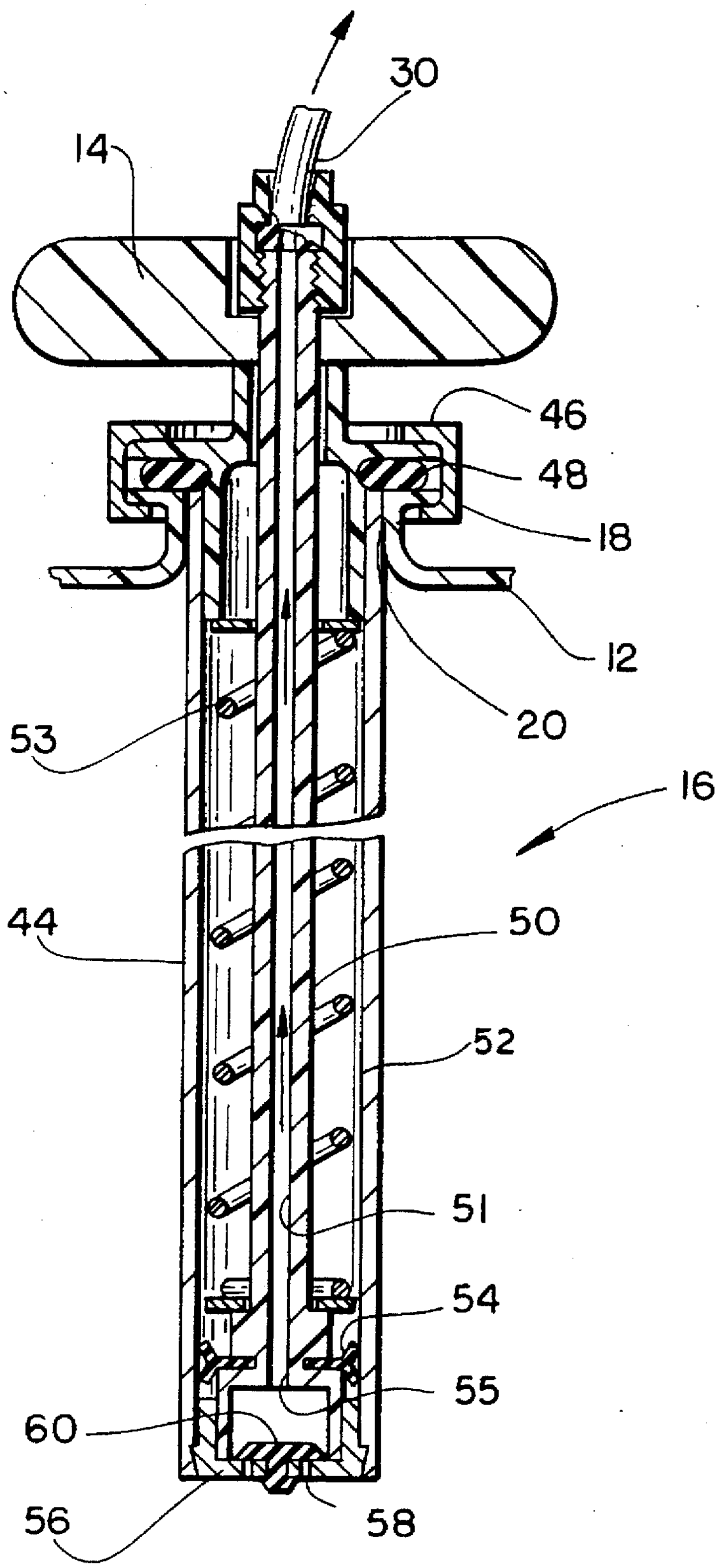
FIG. 5 is a further enlarged longitudinal sectional view of the pump assembly.
Figure 6:
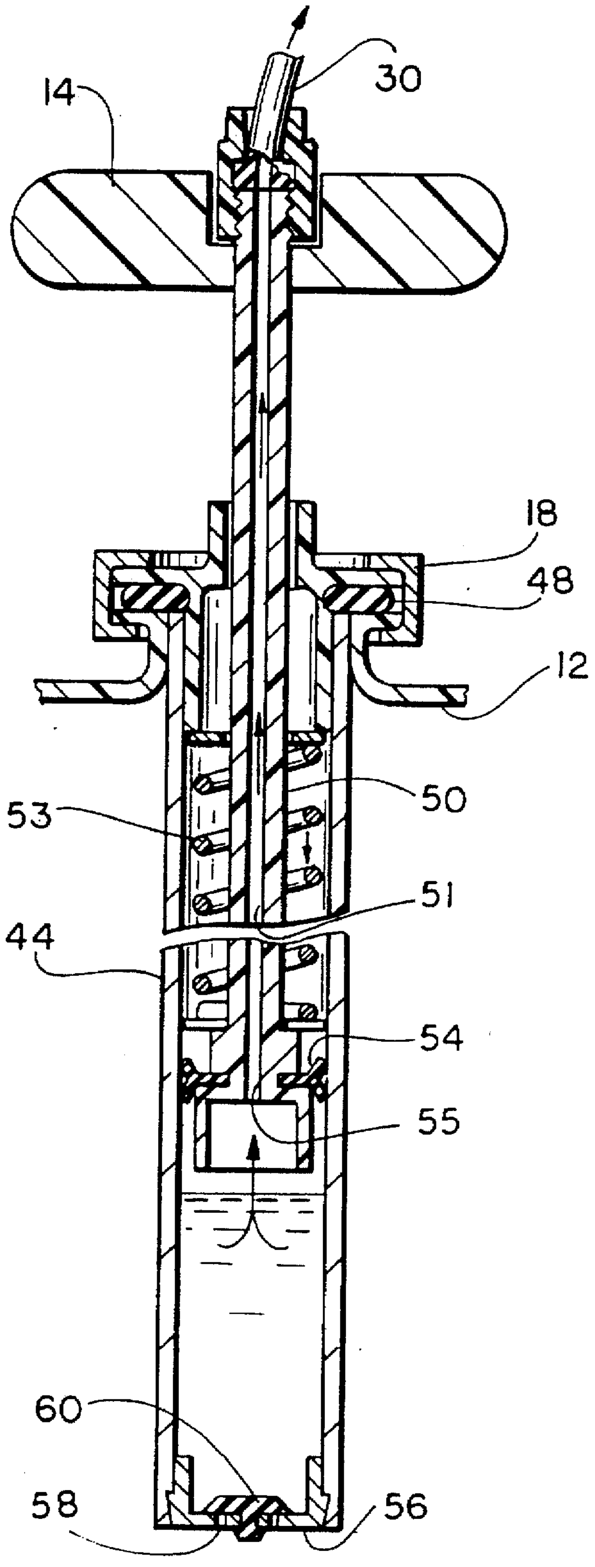
FIG. 6 is a similar view showing the pump during its intake stroke.

In the drawing, the sprayer package 10 as supplied to the consumer is illustrated in FIGS. 1 and 2. In this condition the tank 12 of a suitable plastic is not pressurized but contains the diluted chemical solution to be sprayed and is also suitably sealed so as to be a so called "shipper". Towards this end, the pump handle 14 will be suitably releasably secured in place for example, by tape, shrink wrap or any suitable releasable clip or fastener. The pump assembly. 16 and, specifically, the top cap 18 on the pump cylinder will be suitably sealed and secured to the tank 12 across a fill opening but only after the tank 12 is filled. In this regard, the tank 12, may be formed by blow molding from a suitable resin.

The hose 30 and spray control valve 32 may be conveniently sealably secured to the pump handle 14 and all are placed as shown and perhaps secured in place by tape, shrink wrap or other suitable fastening means. The shrink wrap label 34 extending circumferentially around the tank 12 within the circumferential recess 35 conveniently secures the extension rod 36 and discharge nozzle 38 within the longitudinal cavity 40. Thus, the sprayer package 10 depicted in FIGS. 1 and 2 will be marketed and sold as shown with a contained chemical, preferably not under pressure, ready for spraying in the same fashion as and along with bottles of such solution or chemical concentrate.

Once the sprayer package 10 is purchased, the consumer prepares it for spraying by removing the fastening means holding the pump handle 14, hose 30 and control valve 32 and then freeing extension rod 36 and nozzle 38. The pump assembly 16 is then activated.

Referring now to pump assembly 16, it will be observed that pump cylinder 44 is suitably secured and sealed across opening 20 by the top cap 18. Cap 18 is, in turn, threadably secured and sealed across opening 20 defined by raised externally threaded neck 46 of the tank 12. Piston rod 50 having through bore 51 extends downwardly from the handle 14 and is slidable within bore 52 of the top cap 18. A preloaded spring 53 surrounds the rod 50 and is biased against the cap 18 and piston 54. The lower end of rod 50 mounts piston 54 having through bore 55 engaging the inner wall of the cylinder 44. The lower end of the cylinder 44 has secured thereto a plug 56 having openings 58 covered by the umbrella valve 60. Pulling the handle up retracts the piston against the bias of spring 53 opening valve 60 drawing liquid into the cylinder through the openings 58 from the interior of tank 12. The spring 53 will be compressed and when the handle 14 is released, valve 60 closes the opening 58, and the piston 54 is urged toward the plugged end of the cylinder to pressurize the liquid in the cylinder. Liquid will then be forced out through the bores 55 and 511 into hose 30. Since the spring 53 is preloaded, pressure is maintained until essentially all the liquid in the cylinder 44 is dispensed.

The valve 32 is advantageously selected for its simplicity of structure and operation. Thus, valve 32 can simply be an IV type of valve in which the hose 30 extends with the flexible arm adapted to pivot from an outer position at which the bore of the hose 30 is opened to several intermediate inner positions at which the hose is squeezed to restrict the bore opening and eventually to a fully closed position at which the bore is completely shut.

Accordingly, this valve 32 may include a handle 74 through which the hose 30 extends. The rod 36 may be conveniently attached to the distal end of the handle as shown. Flexible arm 76 may be depressed from a fully extended position at which the hose 30 is not pinched to a depressed position at which the hose 30 is squeezed to decrease the size of the hose bore to restrict liquid flow to a fully depressed position at which the bore is closed. Obviously other types of flow control valves may be deployed.

As previously explained the hose 30 also extends within and through the rod 36 and is coupled in any suitable manner with nozzle 38 selected to provide the desired discharge pattern. Where desired or necessary a cone 78 may be associated with discharge nozzle 38.

In order to assure the dispensing of the entire contents of the tank 12, an angled handle 80 is integrally formed on the tank 12 and is so disposed and oriented such that when the handle 80 is held, the tank 12 will tip forwardly to place the base of the cylinder 44 at the lowest most position relative to the remaining parts of the tank 12. In this regard, the angled handle 80 has a gripping part at an angle less than 90° relative to the vertical axis of the cylinder 44.

In order to keep the costs of the sprayer package 10 at a minimum, all parts are formed of a suitable resin.

Figure 7:
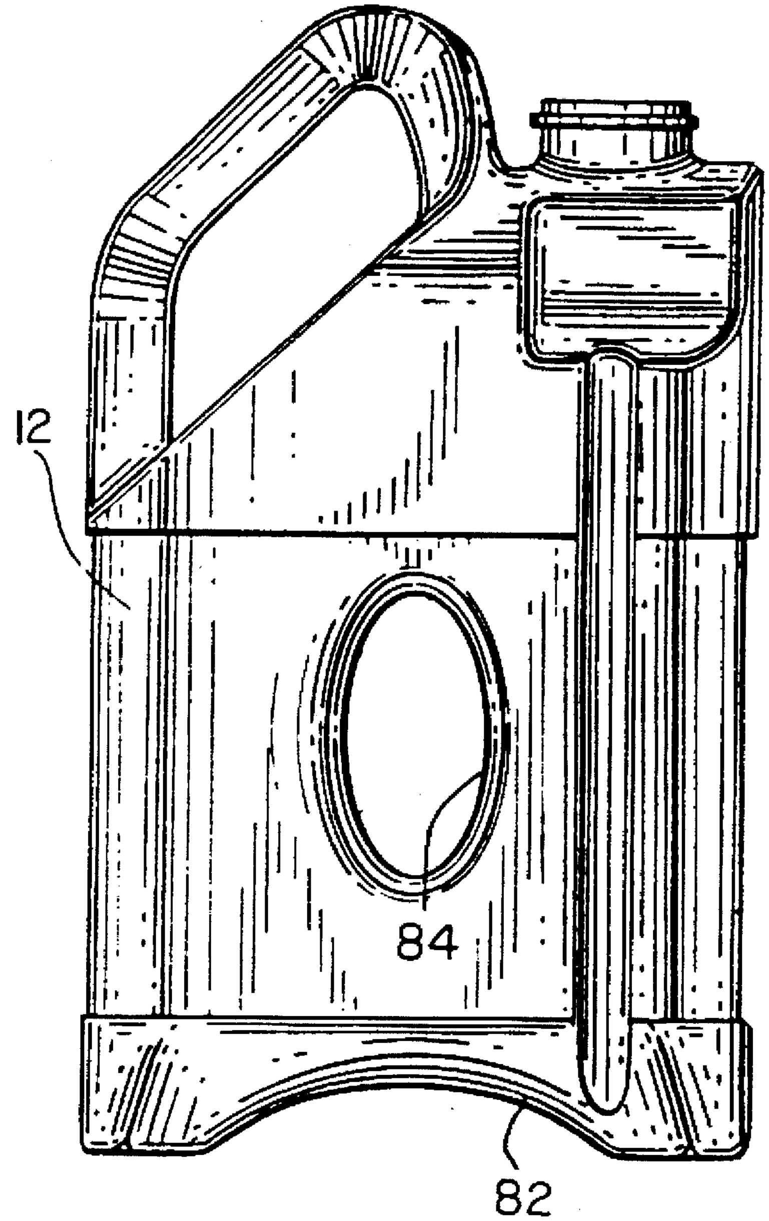
FIG. 7 is a front elevational view showing another embodiment of the sprayer tank.

The present invention also contemplates strengthening tank 12 to ensure its integrity as inexpensively as possible. In this connection, the base is formed with a reverse dome 82 to prevent ballooning and cross member 84 (see FIG. 7) is blow molded into the tank to prevent bowing of the tank sides. The bowing of the sides and ballooning of the base occur as a result of the weight of the liquid inside the tank 12.

It is contemplated that the sprayer of this invention has only limited use after the contents of the tank 12 has been emptied. In this regard, should the consumer attempt to remove the cap 18, the cap 18 will be destroyed, ruptured or rendered useless so that it cannot be recoupled to the threaded neck 46. The customer will then be required to purchase a refill container with the chemical solution to be sprayed which will have another cap 18. The pump cylinder will have to be removed in order to fill the tank 12 and replaced before applying the new cap 18.

In order to further insure only limited reuse of the sprayer 10, other options are contemplated by the present invention which can be incorporated individually or in combination. For example, spring 53 may have a limited life and will fail after a preset number of reciprocations. A filter (not shown) may be conveniently incorporated anywhere from the pump inlet to nozzle outlet which filter will become fouled with particulate matter in the chemical solution in the tank 12; or the filter material will be reactive with some element or ingredient of the solution. Another approach would be to have a plug (not shown) or any component between the pump inlet to the nozzle outlet that will dissolve over time upon contact with the chemical solution in the tank 12. A mechanical counting mechanism (not shown) can be associated with any of the components of the sprayer, that is exposed to repeated usage which will allow use and operation a specified number of times before lock-up. A piston seal or valve seal failure is also contemplated which will produce failure after some number of cycles; or the seal valve piston can erode or swell by being chemically sensitive to the chemical solution in the tank 12 so that after certain usage the part will swell, erode or fail to function. A further embodiment is to have threads fail or wear out after a number of uses such as the cap 18 or threaded neck 46. Of course, the cap 18 could fail after a certain number of uses. The spray control valve 32 could be designed to break, close or open, or otherwise fail after a certain number of activations.

Thus, the several aforenoted objects and advantages are most effectively obtained. Although a single somewhat preferred embodiment has been disclosed and described in detail herein, it should be understood that this invention is in no sense limited thereby and its scope is to be determined by that of the appended claims.

We claim:

1. A limited time use sprayer comprising:

a plastic tank having an exterior having a top and base and an interior for liquid to be dispensed;

an inlet at the tank top for filling the tank with liquid;

an outlet at the tank top for the liquid contained in the tank;

pump means for forcing the liquid out the outlet under pressure, the pump means including a cylinder and piston movable in the cylinder, the piston having a piston rod having an outer end extending exteriorly of the tank top and a handle on the outer end of the piston rod the cylinder being disposed in the tank and having an outer end and an inner end, the tank having surfaces proximal the cylinder outer end;

a hose having a proximal end extending from the tank outlet and having a distal end;

a control valve associated with the hose for controlling an amount of discharge of the liquid that is sprayed;

a discharge nozzle and rod means coupled with the distal end of hose for the selected discharge pattern of the liquid to be sprayed; and failure means interposed between the cylinder inner end and discharge nozzle for failing after a predetermined time and use to render the sprayer nonfunctional so that the sprayer cannot be reused.

2. The invention in accordance with claim 1 where an angled handle extends upwardly and integrally from the tank and is so constructed and arranged so that when gripped, the tank will tilt to permit all of the liquid in the tank to be removed by spraying.

3. The invention in accordance with claim 1 wherein a longitudinal cavity is formed on exterior of the tank, an extension rod is coupled with the discharge nozzle and the rod being disposed in the cavity and secured therein prior to purchase and use thereof by a customer.

4. The invention in accordance with claim 1 wherein the tank has a base, a reverse dome integrally molded in the base for strengthening the base and prevent ballooning thereof.

5. The invention in accordance with claim 1 wherein the exterior of the tank is slightly recessed about its circumference to receive a shrink wrapped label.

6. The invention in accordance with claim 1 wherein the tank inlet is defined by raised surfaces of the tank defining an opening, the cylinder outer end being connected with the raised surfaces, a cap extending over the cylinder outer end and tank inlet and being connected to both the cylinder outer end and the raised surfaces of the tank.

7. The invention in accordance with claim 1 wherein the control valve includes a handle having a passageway, the hose extending through the passageway of the handle, a pivotal arm on the handle adapted to be pivoted away from the hose and towards the hose to pinch the hose and restrict the flow of liquid therein.

8. The invention in accordance with claim 7 wherein an extension rod is connected to the handle and extends around the hose and is coupled with the discharge nozzle.

9. A limited time use sprayer comprising:

a tank having an exterior and an interior for liquid to be dispensed;

an inlet at the tank top for filling the tank with liquid;

an outlet for the liquid contained in the tank;

pump means for forcing the liquid out the outlet under pressure, the pump means including a cylinder and piston movable in the cylinder, the cylinder being disposed in the tank and having an outer end and an inner end, the tank having surfaces proximal the cylinder outer end;

a hose having a proximal end extending from the tank outlet and having a distal end;

a control valve associated with the hose for controlling an amount of discharge of the liquid that is sprayed;

a discharge nozzle coupled with the distal end of hose for the selected discharge pattern of the liquid to be sprayed; and failure means interposed between the cylinder inner end and discharge nozzle for failing after a predetermined time and use to render the sprayer nonfunctional so that the sprayer cannot be reused, the tank having side walls and a through hole integrally molded in the tank to join the side walls and prevent bowing thereof.

10. A limited time use sprayer comprising:

a tank having an exterior and an interior for liquid to be dispensed;

an inlet at the tank top for filling the tank with liquid;

an outlet for the liquid contained in the tank;

pump means for forcing the liquid out the outlet under pressure, the pump means including a cylinder and piston movable in the cylinder, the cylinder being disposed in the tank and having an outer end and an inner end, the tank having surfaces proximal the cylinder outer end;

a hose having a proximal end extending from the tank outlet and having a distal end;

a control valve associated with the hose for controlling an amount of discharge of the liquid that is sprayed;

a discharge nozzle coupled with the distal end of hose for the selected discharge pattern of the liquid to be sprayed; and failure means interposed between the cylinder inner end and discharge nozzle for failing after a predetermined time and use to render the sprayer nonfunctional so that the sprayer cannot be reused, the cylinder of the pump means having an interior surface, a plug at the cylinder inner end and having a plurality of openings, an umbrella valve extending over and closing the openings and adapted to flex to open the openings, the piston having a piston rod having an outer end extending exteriorly of the tank and a handle on the outer end of the piston rod, a preloaded spring disposed about the piston rod and biased against the piston and surfaces proximal the outer end of the cylinder, the piston engaging interior surfaces of the cylinder and adapted to be retracted by pulling on the handle and to compress the spring and released under the force of the spring, a bore extending through the piston and piston rod into the hose, when the piston is released and umbrella valve closes the openings and the space between the piston and plug is pressurized by the force of the spring to force the liquid through the bores into the hose under pressure and when the piston is retracted the umbrella valve flexes to open the openings in the plug to draw liquid into the space between the piston and plug.

11. A sprayer comprising:

a tank having an exterior and an interior for liquid to be dispensed;

an inlet for filling the tank with the liquid;

an outlet for the liquid contained in the tank;.

a hose having a proximal end extending from the tank outlet and having a distal end;

a control valve associated with the hose for controlling the amount of discharge of the liquid that is sprayed;

a discharge nozzle coupled with the distal end of the hose for the selected discharge pattern of the liquid to be sprayed;

pump means for forcing the liquid out the outlet under pressure, the pump means including a cylinder and piston movable in the cylinder, the cylinder being disposed in the tank and having an outer end, the tank having surfaces proximal the cylinder outer end; and wherein the cylinder of the pump means having an interior surface, a plug at the cylinder inner end and having a plurality of openings, an umbrella valve extending over and closing the openings and adopted to flex to open the openings, the piston having a piston rod having an outer end extending exteriorly of the tank and a handle on the outer end of the piston rod, a preloaded spring disposed about the piston rod and biased against the piston and surfaces proximal the outer end of the cylinder, the piston engaging the interior surfaces of the cylinder and adapted to be retracted by pulling on the handle and to compress the spring and released under the force of the spring, a bore extending through the piston and piston rod into the hose, when the piston is released the umbrella valve closes the openings and the space between the piston and plug is pressurized by the force of the spring to force the liquid through the bores into the hose under pressure and when the piston is retracted the umbrella valve flexes to open the openings in the plug to draw liquid into the space between the piston and plug.

12. The invention in accordance with claim 11 wherein an angled handle extends upwardly and integrally from the tank and is so constructed and arranged so that when gripped, the tank will tilt to permit all of the liquid in the tank to be removed by spraying.

13. The invention in accordance with claim 11 wherein a longitudinal cavity is formed on the exterior of the tank, an extension rod is coupled with the discharge nozzle and the rod being disposed in the cavity and secured therein prior to purchase and use thereof by a customer.

14. The invention in accordance with claim 11 wherein the tank has a base, a reverse dome integrally molded in the base for strengthening the base and prevent ballooning thereof.

15. The invention in accordance with claim 11 wherein the exterior of the tank is slightly recessed about its circumference to receive a shrink wrapped label.

16. The invention in accordance with claim 11 wherein the tank has side walls and a through hole is integrally molded in the tank to join the side walls and prevent bowing thereof.

17. The invention in accordance with claim 11 wherein the tank inlet is defined by raised surfaces of the tank defining an opening, the cylinder outer end being connected with the raised surfaces, a cap extending over the cylinder outer end and tank inlet and being connected to both the cylinder outer end and the raised surfaces of the tank.

18. The invention in accordance with claim 11 wherein the control valve includes a handle having a passageway, the hose extending through the passageway of the handle, a pivotal arm on the handle adapted to be pivoted away from the hose and towards the hose to pinch the hose and restrict the flow of liquid therein.

19. The invention in accordance with claim 18 wherein an extension rod is connected to the handle and extends around the hose and is coupled with the discharge nozzle.

20. The invention in accordance with claim 19 wherein an angled handle extends upwardly and integrally from the tank and is so constructed and arranged so that when gripped, the tank will tilt to permit all of the liquid in the tank to be removed by spraying;

a longitudinal cavity being formed on the exterior of the tank, an extension rod being coupled with the discharge nozzle and the rod being disposed in the cavity and secured therein prior to purchase and use thereof by a customer;

the tank having a base, a reverse dome integrally molded in the base for strengthening the base and prevent ballooning thereof;

the exterior of the tank being slightly recessed about its circumference to receive a shrink wrapped label;

the tank having side walls and a through hole being integrally molded in the tank to join the side walls and prevent bowing thereof;

the tank inlet being defined by raised surfaces of the tank defining an opening, the cylinder outer end being connected with the raised surfaces, a cap extending over the cylinder outer end and tank inlet and being connected to both the cylinder outer end and the raised surfaces of the tank.

21. A limited time use sprayer comprising:

a vertically upright plastic tank having an exterior having a top and an interior for liquid to be dispensed and the tank having a base adopted to rest on a horizontal surface whereby the tank is in an upright vertical position;

an inlet at the tank top for filling the tank with liquid;

an outlet at the tank top for the liquid contained in the tank;

pump means for forcing the liquid out the outlet under pressure, the pump means including a cylinder having a vertical axis and piston movable in the cylinder the piston having a piston rod having an outer end extending exteriorly of the tank top and a handle on the outer end of the piston rod, the cylinder being disposed in the tank and having an outer end and an inner end, the tank having surfaces proximal the cylinder outer end;

a hose having a proximal end extending from the tank outlet and having a distal end;

a control valve associated with the hose for controlling the amount of discharge of the liquid that is sprayed;

a discharge nozzle and rod means coupled with the distal end of the hose for the selected discharge pattern of the liquid to be sprayed; and an angled handle extending upwardly and integrally from the tank and is so constructed and arranged so that when gripped, the tank will tilt from its vertical upright position to permit all of the liquid in the tank to be removed by spraying, the angled handle having a gripping part at an angle less than 90 degrees relative to the vertical axis.

22. A limited time use sprayer comprising:

a plastic tank having an exterior having a top and base and an interior for liquid to be dispensed;

an inlet at the tank top for filling the tank with liquid;

an outlet at the tank top for the liquid contained in the tank;

pump means for forcing the liquid out the outlet under pressure, the pump means including a cylinder and piston movable in the cylinder, the piston having a piston rod having an outer end extending exteriorly of the tank top and a handle on the outer end of the piston rod, the cylinder being disposed in the tank and having an outer end and an inner end, the tank having surfaces proximal the cylinder outer end;

a hose having a proximal end extending from the tank outlet and having a distal end;

a control valve associated with the hose for controlling the amount of discharge of the liquid that is sprayed;

a discharge nozzle and rod means coupled with the distal end of the hose for the selected discharge pattern of the liquid to be sprayed; and the exterior of the tank being slightly recessed about its circumference and a shrink wrapped label being disposed therein.

23. A limited time use sprayer comprising:

a plastic tank having an exterior having a top and base and an interior for liquid to be dispensed;

an inlet at the tank top for filling the tank with liquid;

an outlet at the tank top for the liquid contained in the tank;

pump means for forcing the liquid out the outlet under pressure, the pump means including a cylinder and piston movable in the cylinder, the piston having a piston rod having an outer end extending exteriorly of the tank top and a handle on the outer end of the piston rod, the cylinder being disposed in the tank and having an outer end and an inner end, the tank having surfaces proximal the cylinder outer end;

a hose having an integral proximal end extending from the tank outlet and having a distal end;

a control valve associated with the hose for controlling the amount of discharge of the liquid that is sprayed;

a discharge nozzle and rod means coupled with the distal end of the hose for the selected discharge pattern of the liquid to be sprayed; and the control valve including a handle having a passageway, the hose extending through the passageway of the handle, means on the handle adapted to be moved away from the hose and towards the hose to pinch the hose and restrict the flow of liquid therein.

24. A limited time use sprayer comprising:

a tank having an exterior and an interior for liquid to be dispensed;

an inlet for filling the tank with the liquid; an outlet for the liquid contained in the tank;

pump means for forcing the liquid out the outlet under pressure, the pump means including a cylinder and piston movable in the cylinder, the cylinder being disposed in the tank and having an outer end and an inner end, the tank having surfaces proximal the cylinder outer end;

a hose having a proximal end extending from the tank outlet and having a distal end;

a control valve associated with the hose for controlling the amount of discharge of the liquid that is sprayed;

a discharge nozzle coupled with the distal end of the hose for the selected discharge pattern of the liquid to be sprayed; and wherein the cylinder of the pump means having an interior surface, the cylinder inner end having a plurality of openings, an umbrella valve extending over and closing the openings and adapted to flex to open the openings, the piston having a piston rod having an outer end extending exteriorly of the tank and a handle on the outer end of the piston rod.

* * * * *